United States Patent [19]

Saurino et al.

[11] 4,263,278
[45] Apr. 21, 1981

[54] MORTUARY COMPOSITION

[76] Inventors: Vincent R. Saurino, 1099 Banyan Rd.; Bruce C. Saurino, 480 NW. 20th St., Apt. #214, both of Boca Raton, Fla. 33432

[21] Appl. No.: 56,308

[22] Filed: Jul. 10, 1979

[51] Int. Cl.³ ................................. A01N 1/00
[52] U.S. Cl. ....................................... 424/75
[58] Field of Search ............................ 424/75

[56] References Cited

U.S. PATENT DOCUMENTS

| | | | |
|---|---|---|---|
| 2,272,525 | 2/1942 | Jones | 424/75 |
| 2,555,504 | 6/1951 | Noll | 424/75 |
| 2,880,134 | 3/1959 | Robinette | 424/75 |

FOREIGN PATENT DOCUMENTS 1301316 12/1972 United Kingdom .

*Primary Examiner*—Ethel G. Love
*Attorney, Agent, or Firm*—Kenyon and Kenyon

[57] ABSTRACT

The present invention relates to a method for embalming the body of a deceased human being, and to materials for use therein. More specifically, the invention provides a method in which a composition comprising certain specified quaternary ammonium compounds is applied to the skin of the body for the purposes of preventing decay, preventing the growth and spread of disease-causing organisms and retaining life-like appearance.

12 Claims, No Drawings

MORTUARY COMPOSITION

This application is a continuation-in-part of application Ser. No. 571,398, filed Apr. 24, 1975, now U.S. Pat. No. 4,021,537, issued May 3, 1977.

BACKGROUND OF THE INVENTION

An almost unlimited variety of substances have been applied to bodies for the purpose of embalming. Apart from the role of embalming in the mores of various societies, embalming performs certain practical functions. First, it preserves to a degree, the life-like appearance of the body, so that it may be viewed by mourners for several days, or longer, after death. Second, it prevents the growth of disease causing organisms on the body, which is necessary for the safety of persons who are near the body and who therefore might be infected by those organisms.

By far the most commonly used component to modern embalming fluids is formaldehyde, which is effective in destroying or preventing growth of many disease-causing organisms. However, formaldehyde is not fully satisfactory. For example, there are some disease-causing organisms which can survive formaldehyde. In addition, formaldehyde is a toxic substance and an irritant which can be harmful to embalmers who use it. It has been suspected of being a carcinogen of lung.

Quaternary ammonium compounds are disclosed as embalming materials in U.S. Pat. No. 2,555,504, but the compounds disclosed are not believed to have been particularly effective.

SUMMARY OF INVENTION

The present invention provides a composition for surface application to bodies which is free of the toxic effects associated with formaldehyde, but which nevertheless fulfills the requirements of an embalming fluid. It includes a mixture of certain quaternary ammonium compounds, and preferably also one of certain tin compounds. In addition, it may include a wetting agent, preferably a non-ionic wetting agent and other compounds described below. The composition is used by applying it to the skin of bodies, and will keep the skin free of harmful organism for several days, or longer, until burial.

DETAILED DESCRIPTION OF PREFERRED EMBODIMENTS

The compositions used in the present invention comprise a mixture of three principal components, designated respectively (A), (B) and (C), as hereinafter defined. In addition, it is preferred that they include a penetrant, an emulsion stabilizer, and a buffer system.

Component A is a synergistic mixture of two selected but dissimilar cationic quaternary ammonium halides which are designated compounds (1) and (2), ordinarily in proportions of 5-95% of (1) to 95-5% of (2), preferably 30 to 80% of (1) with 70-20% of (2) and especially a 50-50 mixture. Compound (1) is an (n-$C_{12-18}$ alkyl) dimethyl benzyl ammonium halide and compound (2) is an (n-$C_{12-14}$ alkyl) dimethyl ethylbenzyl ammonium halide.

Component B is a surfactant or wetting agent selected from the group consisting of cationic, amphoteric and/or non-ionic surfactants; preferably it is a non-ionic surfactant which is pharmaceutically acceptable and which is compatible with the component mixture (A). Particularly preferred are octyl-phenoxy-polyethoxy-ethanol and isoctylphenoxy-polyethoxy-ethanol.

Component C is a water-soluble or water-dispersible organotin compound; preferably it is the ester, tri-n-butyltin oxide, or the organic and halide salts of the ester. Particularly preferred is bis(tri-n-butyltin)oxide.

The following are particularly suitable as compounds (1) and (2): (1) n-alkyl (60% $C_{14}$, 30% $C_{16}$, 5% $C_{12}$, 5% $C_{18}$) dimethyl benzyl ammonium chloride and (2) n-alkyl (68% $C_{12}$, 32% $C_{14}$) dimethyl ethylbenzyl ammonium chloride. As indicated above, compounds (1) and (2) can be admixed in various proportions such that one of said compounds is present in amounts of from 5% to 95% and the other compound makes up the balance, and preferably they can be present in amounts of 30-80% of (1) and 70-20% of (2) or still more preferred is when compounds (1) and (2) are present in essentially equal amounts.

Component B is a surfactant or wetting agent selected from the group of cationic, amphoteric and/or non-ionic surfactants and should be selected for its compatability with components A and C. Component A is not generally compatible with anionic wetting agents and therefore cationic or non-ionic wetting agents are preferred. Compatability is judged by the absence of phase separation when the materials are mixed.

Cationic wetting agents, if used, should be different from the quaternary components making up component A, and can include fatty amine-alkylene oxide reaction products such as the "Ethomeens"; alkyl oxazolidenes prepared by condensing fatty acids with an amino alcohol such as 2-methyl-2-amino-1,3-propanediol and salts thereof; substituted imidazolines formed by reacting fatty acids with alkyl diamines. Typical cationic wetting agents also include "Amine 220," "Alro" amines, "Alkaterge"-O, "Miranol" and "Catiosan", all of which are commercially available surfactants.

The amphoteric wetting agents include condensation products of (1) amino and carboxy compounds, (2) amino and sulfonic esters, (3) amino and alkane sulfonic acids (4) amino and aromatic sulfonic acides, and the like; such as N-dodecyl n:n dimethyl betaine; dodecyl amino proponic acid and their alkali metal salts, etc.

The non-ionic wetting agents, which are preferred, include condensation reaction products of alkylene oxide such as ethylene oxide and/or propylene oxide with fatty alcohols, fatty acids, alkyl phenols such as condensation procedure of octyl or nonyl phenol and ethylene oxide commercially available under the following trade names: "Triton X-100", "Igepal" CA-630 and 710, "Igepal" CO, "Synthetics" B-79, "Neutronyx". Triton X-100, which is the preferred wetting agent is a water soluble octyl–phenoxy–polyethoxy–ethanol containing 10 moles of ethylene oxide per molecule. Still other non-ionic surfactants which can be used include polypropylene glycol, ethylene oxide condensation products available under the trade name of "Pluoronics" such as L-64 and F-68, etc., or the sorbitan esters of fatty acids and their ethylene oxide derivatives which are available commercially under the trade names of "Spans" and "Tweens" and include sorbitan monostearate (Span 60), sorbitan monoleate palmitate (Span 40), sorbitan monolaurate (Span 20) and the "Tweens" such as polyoxyethylene sorbitan monostearate (Tween 61), polyoxyethylene sorbitan tristerate (Tween 65), polyoxyethylene sorbitan trioleate (Tween 85) and the like.

The tin compounds used as components c, are water-soluble and/or water dispersible esters of bis (tri-n-butyltin) oxide. Tri-n-butyltin benzoate has been found to be particularly useful. However, other water-soluble and/or water-dispersible esters with inorganic halide acids or organic aliphatic and aromatic acids may be used, particularly with lower saturated aliphatic and aromatic monocarboxylic acids, for example tri-n-butyltin salicylate, bis (tri-n-butyltin) silicofluoride, tri-n-butyltin butyrate, and others. Alternatively, the triorganotin compounds used as components C can vary in the organic group of the molecule. For example, the esters and salts of triamyltin, triethyltin, trimethyltin, tripropyltin, and triphenyltin oxides and others may be used.

The tin compound is not essential to the compositions. However, without them, the compositions are not completely effective against certain organisms such as *Trichophyton mentagrophytes*, and related species, Microsporum and various species, Epidermaphyton and various species, *Staphylococcus aureus, Candida albicans,* Neisseria species, and saprophytic molds, especially Aspergillus.

In the preferred forms of the invention, the compositions also include a penetrant, an emulsion stabilizer, and a buffer system. The materials used for these purposes are, respectively, isopropyl alcohol, sodium chloride, and acetic acid/sodium acetate. Alternatively, the materials used for an emulsifier and buffer system are hydrochloric acid and sodium acetate. Of course, isopropyl alcohol has disinfecting properties which increase the effectiveness of the compositions slightly.

The overall proportions of the components are subject to some variation from the preferred composition which is described below. Preferred proportions of the effective components are as follows. These proportions are based on amounts of the components and do not include water usually associated with them.

|  |  | Formula 1 |  |  | Formula 2 |  |  |
|---|---|---|---|---|---|---|---|
| Component (A) | (Mixture of Quarternary ammonium compounds) | 0.001 | to | 20% | 0.001 | to | 20% |
| Component (B) | (Surfactant) | 0.001 | to | 5% | 0.001 | to | 5% |
| Component (C) | (Tin ester or salt) | 0 | to | 1% | 0 | to | 1% |
| Penetrant (Isopropyl alcohol) |  | 0 | to | 70% | 0 | to | 70% |
| Emulsion Stabilizer (1) | (Sodium chloride) | 0 | to | 1% | — | to | —% |
| Emulsion Stabilizer (2) | (Hydrochloric acid) | — | to | —% | 0.01 | to | 1% |
| Buffer System (1) | (Acetic acid/Sodium acetate) | 0 | to | 1% | — | to | —% |
| Buffer System (2) | (Sodium acetate) | — | to | —% | 0.01 | to | 1% |

A mixture containing these components is dissolved in water to produce an embalming liquid which contains an active concentration of Component (A) of 0.001 to 20% and corresponding amounts of the other active components.

The following formulation has been selected as particularly suitable.

| FORMULA 1 |  |
|---|---|
| Component (A)-a 50:50 mixture of n-alkyl (60% $C_{14}$, 30% $C_{16}$, 5% $C_{12}$ 5% $C_{18}$) dimethyl benzyl ammonium chloride and n-alkyl (68% $C_{112}$, 32% $C_{14}$) dimethyl ethylbenzyl amonium chloride | 1.0% |
| Component (B) bis (tri-n-butyltin) oxide | 0.1% |
| Component (C) Triton X-100 | 1.0% |
| Isopropyl alcohol | 10.0% |
| Sodium chloride | 0.25% |
| Acetic acid | 0.15% |
| Water | 82.65% |

| -continued |  |
|---|---|
| FORMULA 1 |  |
|  | pH 4.75 |

The following alternative formulation has been selected as also particularly suitable:

| FORMULA 2 |  |
|---|---|
| Component (A)-50:50 mixture of n-alkyl (69% $C_{14}$, 30% $C_{16}$, 5% $C_{12}$, 5% $C_{18}$) dimethyl benzyl ammonium chloride and n-alkyl (68% $C_{12}$, 325 $C_{14}$) dimethyl ethylbenzyl ammonium chloride | 1.0% |
| Component (B) bis(tri-n-butyltin)oxide | 0.1% |
| Component (C) Triton X-100 | 0.5% |
| Isopropyl alcohol | 10.0% |
| Hydrochloric acid | 0.3% |
| Sodium acetate | 0.65% |
| Water | 81.45% |

The composition is simply sprayed and sponged or swabbed onto the surfaces and crevices of a human cadaver, including skin, hair, nails, etc. A sufficient amount is applied to thoroughly wet all surfaces, and allowed to penetrate and dry in the air.

The active components of the composition also are useful for cleaning and filling internal organs of the cadaver as they effectively control organisms which tend to grow there. However, other components are needed to preserve the appearance of the body when they are used.

In the foregoing description, all percentages and proportions are given by weight, unless otherwise stated.

This application contains subject matter related to applicant's issued patent, No. 4,021,537.

It will be appreciated that preferred compositions and methods have been described for purposes of illustration. However, it will be appreciated that changes can be made in details of composition and method of application without departing from the invention, as defined below.

ANTI-MICROBIAL ACTIVITY

The anti-microbial activity of Formulation (1) and Formulation (2) was evaluated on the basis of: (I) AOAC Use Dilution Method, (II) Time Exposure Test, and (III) Practical Field Tests.

I. Method: Use Dilution Method (2) Official Final Action; Methods of Analyses, AOAC, 12th Ed., 1975, pg. 59.

1. Using *Salmonella chloreraesuis* ATCC #10708
2. Using *Staphylococcus aureus* ATCC #6538
3. Using *Pseudomonas aeruginosa* ATCC #15442, Official First Action.

The results were determined at a 95% confidence level over replicate testing. A minimum performance of 59/60 negative carrier subcultures was required. Letheen broth was used as primary and secondary subculture media.

| | I. Results: | | | |
|---|---|---|---|---|
| | FORMULA 1 | | FORMULA 2 | |
| ORGANISM | no. of negative carriers | no. of positive carriers* | no. of negative carriers | no. of positive carriers* |
| *Salmonella choleraesuis* ATCC #10708 | 60 | 0 | 60 | 0 |
| *Staphylococcus aureus* ATCC #6538 | 60 | 0 | 60 | 0 |
| *Pseudomonas aeruginosa* ATCC #15442 | 60 | 0 | 60 | 0 |

*Viability controls were all positive; isolated and confirmed as test organism.

Formula 1 and Formula 2 were found to be effective practical disinfectants at use-dilution.

II. Method: Time Exposure Method. The procedure of Balwant Singh at the Graduate School of Public Health, University of Pittsburgh, was used in a time exposure technique. This method consists of adding a 4 mm loopful of the organism under test, from a 24 hour broth culture (3-4 days in the case of molds and mycobacteria), into 1 ml of the desired dilutions of the formulation. At the designated time intervals, 4 mm loopful samples were transferred from this mixture by streaking onto the agar surface of a proper recovery medium. All plates were incubated for 48 hours and longer for the mold and mycobacteria cultures. The results were recorded and designated by the following scale:

0 = no growth
+ = 10% of normal saline control
++ = 50% of normal saline control
+++ = 75% of normal saline control
++++ = 90+% of normal saline control
digit designations = number of colonies surviving To establish a meaningful appraisal of the broad spectrum antimicrobial activity of the formulation, concentrations were varied in order to attain the end-point of kill for each morphologically and physiologically different type of microorganism. Dilutions, were prepared according to the cell wall structure and resistance of each type of microorganism studied. Representatives of each type were used, inclusive of the gram-negative rods, gram-negative and positive cocci, spore-forming rods, waxy-coated acid-fast, as well as yeast and fungal microorganisms.

| II. Results: End Point of Kill Influence on Varied Organisms | | | | | |
|---|---|---|---|---|---|
| Organism | Dilutions | 5 min | 10 min | 15 min | End Point |
| | 1:1,000 | ++ | 0 | 0 | |
| *Escherichia coli* | 1:1,200 | +++ | ++ | + | 1:1,000 |
| | 1:900 | + | 1 | 0 | |
| *Shigella sonnei* | 1:1,000 | ++ | ++ | 1 | 1:900 |
| | 1:900 | + | 0 | 0 | |
| *Enterobacter cloacae* 1:1,000 | +++ | + | 0 | 1:1,000 | |
| *Proteus Vulgaris* | 1:1,800 | 0 | 0 | 0 | |
| #13315 | 1:2,200 | 3 | 1 | 4 | 1:2,000 |
| | 1:2,500 | ++ | + | 0 | |
| *Bacillus subtilis* | 1:6,000 | 1 | 0 | 0 | |
| #19659 | 1:7,000 | 0 | 0 | 0 | 1:6,000 |
| *Neisseria eatharrhalis* | 1:2,000 | + | 0 | 0 | |
| | 1:4,000 | ++ | + | 0 | 1:2,000 |

| | | Exposure | | | |
|---|---|---|---|---|---|
| Organism | Dilutions | 5 min | 10 min | 15 min | End Point |
| *Mycobacterium* | 1:100 | 1 | 0 | 0 | |
| *smegmatis* ATTC #10143 | 1:400 | 1 | 0 | 0 | 1:400 |
| *Serratia marcescens* | 1:1,000 | + | 0 | 0 | |
| | 1:1,500 | + | 6 | 0 | 1:1,400 |
| *Streptococcus* | 1:1,800 | 0 | 1 | 0 | |
| *faecalis* | 1:2,200 | + | + | 0 | 1:2,000 |
| | 1:2,500 | ++ | + | 0 | |
| *Streptococcus* | 1:6,000 | 6 | 0 | 0 | |
| *pyogenes* | 1:12,000 | 0 | 0 | 0 | 1:1,000 |
| *Klebsiella pneumoniae* | 1:1,000 | 0 | 0 | 0 | |
| ATCC #10031 | 1:1,500 | ++ | + | 4 | 1:1,250 |
| *Candida albicans* | 1:1,600 | 0 | 0 | 0 | |
| ATCC #10259 | 1:1,800 | 6 | 3 | 0 | |
| | 1:2,200 | + | 5 | 0 | |
| | 1:2,500 | + | + | 3 | 1:1,800 |
| *Salmonella* ATCC #10708 | 1:1,200 | 0 | 0 | 0 | |
| *cholerae-suis* | 1:1,400 | +++ | ++ | + | 1:1,300 |
| *Salmonella* | 1:700 | ++ | 0 | 0 | |
| *typhimurium* | 1:900 | ++++ | ++++ | ++ | 1:800 |
| *Staphylococcus aureus* | 1:1,000 | + | 0 | 0 | |
| ATCC #6538 | 1:1,100 | ++++ | + | 1 | 1:1,000 |
| *Staphylococcus* | 1:1,500 | 0 | 0 | 0 | |
| *epidermidis* | 1:2,000 | + | 4 | 0 | 1:1,800 |
| | 1:3,000 | + | 4 | 1 | |
| *Pseudomonas* ATCC #15442 | 1:80 | 0 | 0 | 0 | |
| *aeruginosa* | | ++++ | + | 4 | 1:90 |
| *Pseudomonas sp.* | 1:500 | 0 | 0 | 0 | |
| (equine isolate) | 1:1,000 | + | + | 14 | 1:750 |

This preparation is unusually effective against spore-forming organisms such as *Bacillus subtilis* and *Candida*

*albicans*—(dilutions of 1:6,000 and 1:1,800). It is equally efficacious with the gram-positive and most of the gram-negative organisms. Those gram-negative rods with complex mucopolysaccharide molecules composing their cell walls are especially resistant to all forms of disinfectants, antiseptics, and antibiotics. The most classic of these resistant forms is *Pseudomonas aeruginosa*. This formulation can be diluted almost 100 times and it still will maintain its killing effect on this organism.

III. Method: Practical Field tests. Tests were conducted at the Miami-Dade Community College, School of Mortuary Science by a licensed member of the embalming teaching staff. A total of 112 practical field tests were conducted. Cases reported included (confirmed):
3 Pulmonary tuberculosis
1 meningitis Meningococcal
14 Staphylococcal infections
6 Pseudomonal infections Prior to the preparation of the remains for embalming, various areas of the body known to harbor microorganisms were cultured as controls. Following routine preparation, application of said disinfectant, and embalming, subsequent cultures were taken at various convenient time intervals prior to release of the remains.

The culture technique employed was to swab the area in question with a cotton-tipped swab pre-moistened in physiological saline using aseptic technique. The swab was then transferred to Letheen broth and incubated 48 hours at 37° C. Results were recorded as growth or no growth.

III. Results: The results are summarized in the following table:

| Agent | Normal or Specific Area | Spray only | 1 | 2 | 3 | 4 | 5 | Spray & Swab | 1 | 2 | 3 | 4 |
|---|---|---|---|---|---|---|---|---|---|---|---|---|
| Formula #1 | mouth | X | + | + | + | + | | X | + | 0 | 0 | 0 |
| at use-dilution | nose | X | + | + | + | + | | X | + | 0 | 0 | 0 |
| (50 cases) | eyes | X | + | 0 | 0 | 0 | | X | + | 0 | 0 | 0 |
| | rectum (1"depth) | X | + | + | + | + | | X | + | 0 | 0 | 0 |
| | genitals | X | + | 0 | 0 | 0 | | X | + | 0 | 0 | 0 |
| | arm pits | X | + | 0 | 0 | 0 | | X | + | 0 | 0 | 0 |
| | groin | X | + | 0 | 0 | 0 | | X | + | 0 | 0 | 0 |
| Formula #2 | mouth | X | + | + | + | + | | X | + | 0 | 0 | 0 |
| at use-dilution | nose | X | + | + | + | + | | X | + | 0 | 0 | 0 |
| (50 cases) | eyes | X | + | 0 | 0 | 0 | | X | + | 0 | 0 | 0 |
| | rectum (1"depth) | X | + | + | + | + | | X | + | 0 | 0 | 0 |
| | genitals | X | + | 0 | 0 | 0 | | X | + | 0 | 0 | 0 |
| | arm pits | X | + | 0 | 0 | 0 | | X | + | 0 | 0 | 0 |
| | groin | X | + | 0 | 0 | 0 | | X | + | 0 | 0 | 0 |
| Formula #1 | mouth | X | + | + | + | + | | X | + | 0 | 0 | 0 |
| at use-dilution | nose | X | + | + | + | + | | X | + | 0 | 0 | 0 |
| (12 cases) | eyes | X | + | 0 | 0 | 0 | 0 | X | + | 0 | 0 | 0 |
| | rectum (1"depth) | X | + | + | + | + | + | X | + | 0 | 0 | 0 |
| | genitals | X | + | 0 | 0 | 0 | 0 | X | + | 0 | 0 | 0 |
| | arm pits | X | + | 0 | 0 | 0 | 0 | X | + | 0 | 0 | 0 |
| | groin | X | + | 0 | 0 | 0 | 0 | X | + | 0 | 0 | 0 |

Where the digits 1 through 5, in the heading, represent the following:
Digit:
1. Culture taken prior to prep (control)
2. After embalming ⅔ hours
3. Twelve hours
4. Twenty-four hours
5. Twenty-four + at release
+ Growth
0 No Growth Conclusions:
1. Effectiveness directly related to method of application
2. Compatible with liquid soap
3. Effective disinfectant surface cleaning agent.
4. Does not leave viewable film on disinfected areas.
5. No toxic responses (evidence of rash, or skin or mucous membrane irritation) among any of the many Mortuary Science students who applied this formulation over the six months of this test period.

Method:
Ten rats, five male and five female, weighing between 200 and 300 grams each, were fed a level of 5 ml per kilo of the said composition.
Results:

| No. Fed | No. Dead |
|---|---|
| 10 | 0 |

The said composition is not a toxic one as defined in CFR 16:1500. 3(c)(2)(i).

We claim:
1. A method of preserving and embalming a human cadaver which comprises applying thereto a composition comprising as active ingredients:
   (a) a synergistic mixture of about 5–95% of an n-$C_{12-18}$-alkyl-dimethyl-benzyl-ammonium halide and about 95–5% of an n-$C_{12-14}$-dimethyl-ethylbenzyl-ammonium halide,
   (b) a water soluble or water dispersible ester of bis-(tri-n-butyl-tin)-oxide; there being about 1–200 parts of (a) for each part of (b); and
   (c) a non-ionic surface active agent in an amount of about at least 0.05% and up to 30 times the amount of (a) and (b), wherein said composition is adapted and applied to be biologically active against a wide variety of organisms.

2. A method according to claim 1, wherein the synergistic mixture of (a) is about 30 to 80% of n-$C_{12-18}$-alkyl-dimethyl-benzyl-ammonium halide and about 70 to 20% n-$C_{12-14}$-alkyl-dimethyl-ethylbenzyl ammonium halide.

3. A method according to claim 1, wherein the synergistic mixture of (a) is about 50% of n-$C_{12-18}$-alkyl-dimethyl-benzyl-ammonium halide and about 50% of n-$C_{12-14}$-alkyl-dimethyl-ethyl-benzyl-ammonium halide.

4. A method according to claim 1, wherein said synergistic mixture consists essentially of about equal amounts of n-alkyl-(60% $C_{14}$, 30% $C_{16}$, 5% $C_{12}$, 5% $C_{18}$)-dimethyl-benzyl-ammonium chloride and n-alkyl-(68% $C_{12}$, 32% $C_{14}$)-dimethyl-ethyl-benzyl-ammonium chloride.

5. A method according to claim 1, wherein said ester is (tri-n-butyl-tin) benzoate.

6. The method of claim 1, wherein said non-ionic surfactant is a condensation product of an ethylene oxide and/or propylene oxide.

7. The method of claim 1, wherein said non-ionic surfactant is an octyl-phenoxy-polyethoxy-ethanol.

8. A method as set forth in claim 1 wherein said ester is bis(tri-n-butyltin)oxide.

9. A method as set forth in claim 1 wherein said composition is an aqueous solution.

10. A method as set forth in claim 1 in which said composition contains also a penetrant and an emulsion stabilizer.

11. A method as set forth in claim 1 wherein said composition includes a buffering agent.

12. The method of claim 1 in which the said composition is dispersed through the corpse arterial system concurrently (as a co-injection) with commercially available embalming compositions to arrest putrifactive tissue decay.

* * * * *

UNITED STATES PATENT AND TRADEMARK OFFICE
CERTIFICATE OF CORRECTION

PATENT NO. : 4,263,278                  Page 1 of 2

DATED : April 21, 1981

INVENTOR(S) : Vincent R. Saurino, et al.

It is certified that error appears in the above—identified patent and that said Letters Patent is hereby corrected as shown below:

Column 2, line 4    Delete "organot in" and insert therefor --organotin--.

Column 2, line 25    Delete "compatability" and insert therefor --compatibility--.

Column 2, line 41    Delete "acides" and insert therefor --acids--.

Column 2, line 48    Delete "procedure" and insert therefor --products--.

Column 3, line 63    Delete "$C_{112}$" and insert therefor --$C_{12}$--.

Column 3, line 64    Delete "amonium" and insert therefor --ammonium--.

Column 4, line 14    Delete "325" and insert therefor --32%--.

Column 4, line 19    Insert --pH 4.75%-- below 81.45%.

UNITED STATES PATENT AND TRADEMARK OFFICE
CERTIFICATE OF CORRECTION

PATENT NO. : 4,263,278

DATED : April 21, 1981

INVENTOR(S) : Vincent R. Saurino, et al.

It is certified that error appears in the above—identified patent and that said Letters Patent is hereby corrected as shown below:

Column 6, Table II, for the following organisms should read:

| Organism | Dilutions | 5 min | 10 min | 15 min | End Point |
|---|---|---|---|---|---|
| Enterobacter cloacae | 1:1,000 | +++ | + | 0 | 1:1,000 |
| Neisseria catharrhalis | | | | | |
| Pseudomonas aeruginosa | 1:100 | ++++ | + | 4 | 1:90 |

Column 8, line 59 Insert after "n-$C_{12}$-$C_{14}$-" --alkyl--.

Signed and Sealed this

Twenty-fifth Day of August 1981

[SEAL]

Attest:

GERALD J. MOSSINGHOFF

Attesting Officer

Commissioner of Patents and Trademarks